United States Patent [19]

Krystal

[11] Patent Number: 4,554,254
[45] Date of Patent: Nov. 19, 1985

[54] PROTEIN ASSAY BY SILVER BINDING

[76] Inventor: Gerald Krystal, 1153 E. 19th Ave., Vancouver, B.C., Canada, V6V 1K9

[21] Appl. No.: 682,338

[22] Filed: Dec. 17, 1984

[30] Foreign Application Priority Data

Dec. 4, 1984 [CA] Canada .................................... 469261

[51] Int. Cl.⁴ ...................... G01N 21/78; G01N 33/68
[52] U.S. Cl. ..................................... 436/86; 436/164; 436/175
[58] Field of Search ...................... 436/86, 87, 88, 164, 436/169, 174, 175, 177, 178, 515, 905

[56] References Cited

U.S. PATENT DOCUMENTS 2,594,514  4/1952  Sweet .............................. 436/164 X
4,066,405  1/1978  Henkin ................................... 436/86

OTHER PUBLICATIONS

Lowry et al, *J. Biol. Chem.*, vol. 193, pp. 265–275, 1951.
Weber et al, *J. Biol. Chem.*, vol. 244, No. 16, pp. 4406–4412, 1969.
Bradford, *Anal. Biochem.*, vol. 72, pp. 248–254, 1976.
Switzer et al, *Anal. Biochem.*, vol. 98, pp. 231–237, 1979.
Oakley et al, *Anal. Biochem.*, vol. 105, pp. 361–363, 1980.
Morrissey, *Anal. Biochem.*, vol. 117, pp. 307–310, 1981.
Merril et al, *Anal. Biochem.*, vol. 110, pp. 201–207, 1981.
Giulian et al, *Anal. Biochem.*, vol. 129, No. 2, pp. 277–287, Mar. 1983.
Dion et al, *Anal. Biochem.*, vol. 129, No. 2, pp. 490–496, Mar. 1983.
Schleicher et al, *Anal. Biochem.*, vol. 131, No. 2, pp. 312–317, Jun. 1983.
Ohsawa et al, *Anal. Biochem.*, vol. 135, No. 2, pp. 409–415, Dec. 1983.

*Primary Examiner*—Arnold Turk
*Assistant Examiner*—Robert J. Hill, Jr.
*Attorney, Agent, or Firm*—Christie, Parker & Hale

[57] ABSTRACT

A novel, inexpensive, highly sensitive and quantitative assay for measuring protein in solution based on the capacity of protein to bind silver is described. In this procedure, protein samples are first treated with glutaraldehyde and then exposed to ammoniacal silver. After a specified time, the reaction is terminated by the addition of sodium thiosulfate and the optical density measured at 420 nm. The useful range of the assay for the majority of standard proteins tested lies between 15 and 2000 ng. This represents a 100-fold increase in sensitivity over the Coomassie Brilliant Blue dye binding procedure. There is little or no interference from carbohydrates, non-ionic detergents or ethanol. Pretreatment of protein samples with Bio-Gel P-2 to remove salts, thiol agents, EDTA and SDS, makes this procedure compatible with most commonly used buffers.

19 Claims, 5 Drawing Figures

PROTEIN ASSAY BY SILVER BINDING

FIELD OF THE INVENTION

This invention relates to novel protein analysis technologies and reagents thereof. More particularly, this invention relates to a novel, highly sensitive and quantitative assay for measuring protein in solution based on the capacity of protein to bind silver.

BACKGROUND OF THE INVENTION

Recently a large number of protein and glycoproteins have been identified that appear to mediate cellular proliferation and differentiation processes. See *J. Immunol.* 129, 2431-2436, (1982), Ihle, J. N. et al.; *J. Immunol. Methods* 42, 253-284, (1981) Stanley, E. R., et al.; *J. Biol. Chem.* 252, 5558-5564 (1977) Miyake, T. et al.; *Proc. Natl. Acad. Sci. U.S.A.* 81, 871-875 (1984) Stern, A. S. et al.; and, *Adv. Protein Chem.* 30, 251-451 (1976) Cuatrescasa, P.

Many of these proteins and glycoproteins are active in the $10^{-9}$ to $10^{-13}$ M range. This high potency has facilitated their detection and purification from biological fluids and conditioned media but at the same time has highlighted the need for more sensitive protein determination assays than those currently available. For example, a typical large scale purification of murine Interleukin-3, starting with 150 liters of conditioned medium, yields only 2-10 μg of pure protein. (See Ihle, J. N. et al. above.) Thus, using either, the standard Bradford, *Anal. Biochem.* 72, 248-254, (1976) or Lowry et al. *J. Biol. Chem.* 193, 265-275 (1951) procedures, all of this pure material would have to be sacrificed in order to quantitate accurately the amount of protein present.

In 1976, Bradford successfully adapted the Coomassie protein staining procedure, initially developed for detecting proteins in SDS polyacrylamide gels, *J. Biol. Chem.* 244, 4406-4412 (1969) for quantitating protein levels in solution.

The applicant is aware of the following references which discuss methods of staining proteins in SDS-polyacrylamide gels utilizing the principle of silver binding.

*Anal. Biochem.* 98, 231-237 (1979) Switzer, III, R. C., et al.; *Anal. Biochem.* 105, 361-363 (1980) Oakley, B. R., et al.; *Anal. Biochem.* 110, 201-207 (1981) Merril, C. R., et al.; *Electrophoresis* 2, 135-141 (1981) Sammons, D. W. et al.; *Anal. Biochem.* 117, 307-310 (1981) Morrissey, J. H.; *Anal. Biochem.* 129, 227-287 (1983) Giulian, G. G. et al.; *Anal. Biochem.* 129, 490-496 (1983) Dion, A. S. et al.; *Anal. Biochem.* 131, 312-317 (1983) Schleicher, M., et al.; *Anal. Biochem.* 135, 409-415 (1983) Ohsawa, K., et al.

Useful background references are:
*Handbook of Biochemistry*, Selected Data for Molecular Biology (Sober, H., ed.), Kirschenbaum, D. M. (1970) 2nd ed., pp. C/71-C/98, Chemical Rubber Company, Cleveland, Ohio. *Anal. Biochem.* 55, 166-192 (1973) Kirschembaum, D. M. The use of drained gel permeation beads for desalting protein solutions is described in *Anal. Biochem.* 55, 328-330 (1973) Neal M. W. et al.

SUMMARY OF THE INVENTION

The invention is directed to a novel soluble protein determination assay utilizing the principle of silver binding to protein. The method can be used to quantitate nanogram amounts of protein present in water or in a wide variety of commonly used buffers.

A novel, inexpensive, highly sensitive and quantitative assay for measuring protein in solution based on the capacity of protein to bind silver is described. In this procedure, protein samples are first treated with glutaraldehyde and then exposed to ammoniacal silver. After a specified time, the reaction is terminated by the addition of sodium thiosulfate and the optical density measured at 420 nm. The useful range of the assay for the majority of standard proteins tested lies between 15 and 2000 ng. This represents a 100-fold increase in sensitivity over the Coomassie Brilliant Blue dye binding procedure. There is little or no interference from carbohydrates, non-ionic detergents or ethanol. Pretreatment of protein samples with Bio-Gel P-2 to remove salts, thiol agents, EDTA and SDS, makes this procedure compatible with most commonly used buffers.

The invention is directed to a method of measuring protein in solution comprising: (a) treating a protein sample with a silver-on-protein deposition enhancement agent; (b) exposing the treated protein sample of step (a) above to a silver compound; (c) terminating the exposure reaction of step (b) above after sufficient protein specific colour development has occurred; and (d) measuring the optical density of the exposure terminated sample of step (c) above.

In the method the enhancement agent may be a suitable dialdehyde such as glutaraldehyde. The silver compound may be ammoniacal silver or silver nitrate.

In the method a buffer may be used when colour development interfering ions are present in the protein sample. Gel filtration beads may be used to remove colour development interfering ions in the protein sample.

When gel filtration beads are used to remove colour development interfering ions in the protein sample, minimum levels of ions and detergent may be added to the protein sample to minimize protein loss to the beads.

The concentration of the protein present in the sample may be in the range 10-2000 nanograms. Typically, protein concentration is measured by determining the optical density at 420 nm.

Colour development may be terminated with sodium thiosulfate. Colour development may be terminated at about 10 minutes after commencement of the reaction.

A specific method of measuring protein in solution comprises: (a) treating a protein sample with glutaraldehyde; (b) exposing the glutaraldehyde treated sample to ammoniacal silver; (c) permitting the colour development reaction to proceed for about 10 minutes; (d) terminating the colour development reaction with sodium thiosulfate; and, (e) measuring the optical density of the sample at 420 nm to determine the protein concentration. If the protein sample includes analysis interfering ions, the protein sample is pretreated with drained gel permeation beads.

In one specific embodiment, where no interfering compounds are present in the protein sample, including specific method criteria, the method of measuring protein in solution comprises: (a) diluting a 100 μl aliquot containing 15 to 2000 ng protein to 1 ml with 0.9 ml of distilled water containing 0.02% non-ionic detergent; (b) adding 20 μl of 2.5% glutaraldehyde to the sample prepared by step (a) above; (c) adding 200 μl of ammoniacal silver solution prepared by adding 1.0 ml of 4% w/v sodium hydroxide and 0.2 ml of ammonium hydroxide (29%) to 18.6 ml of distilled water followed by dropwise addition of 0.2 ml of 20% w/v silver nitrate; (d) permitting colour development caused by protein-silver binding to proceed for about 10 minutes; (e) adding 40 μl of 30 mg/ml of sodium thiosulfate to terminate the colour development; and (f) measuring the optical density of the sample at 420 nm.

In another specific embodiment, where interfering compounds are present in the protein sample including specific method criteria, the method of measuring protein in a buffer solution containing an analysis interfering substance comprises: (a) pretreating the protein sample in a buffer solution using gel filtration chromatography; (b) diluting a 100 μl aliquot containing 15 to 2000 ng protein in a buffer containing 0.75% non-ionic detergent, 10 mM Trizma and 10 mM sodium carbonate to 1 ml with 0.9 ml distilled water; (c) adding 20 μl of 2.5% glutaraldehyde to the sample prepared by step (a) above; (d) adding 200 μl of ammoniacal silver solution prepared by adding 1.4 ml of 20% sodium hydroxide and 0.2 ml of concentrated ammonium hydroxide (29%) to 18.2 ml of distilled water followed by dropwise addition of 0.2 ml of 20% w/v silver nitrate; (e) permitting colour development caused by protein-silver binding to proceed for about 10 minutes; (f) adding 40 μl of 30 mg/ml of sodium thiosulfate to terminate colour development; and (g) measuring the optical density of the sample at 420 nm.

DETAILS OF SPECIFIC EMBODIMENTS OF THE INVENTION

Figure 1:
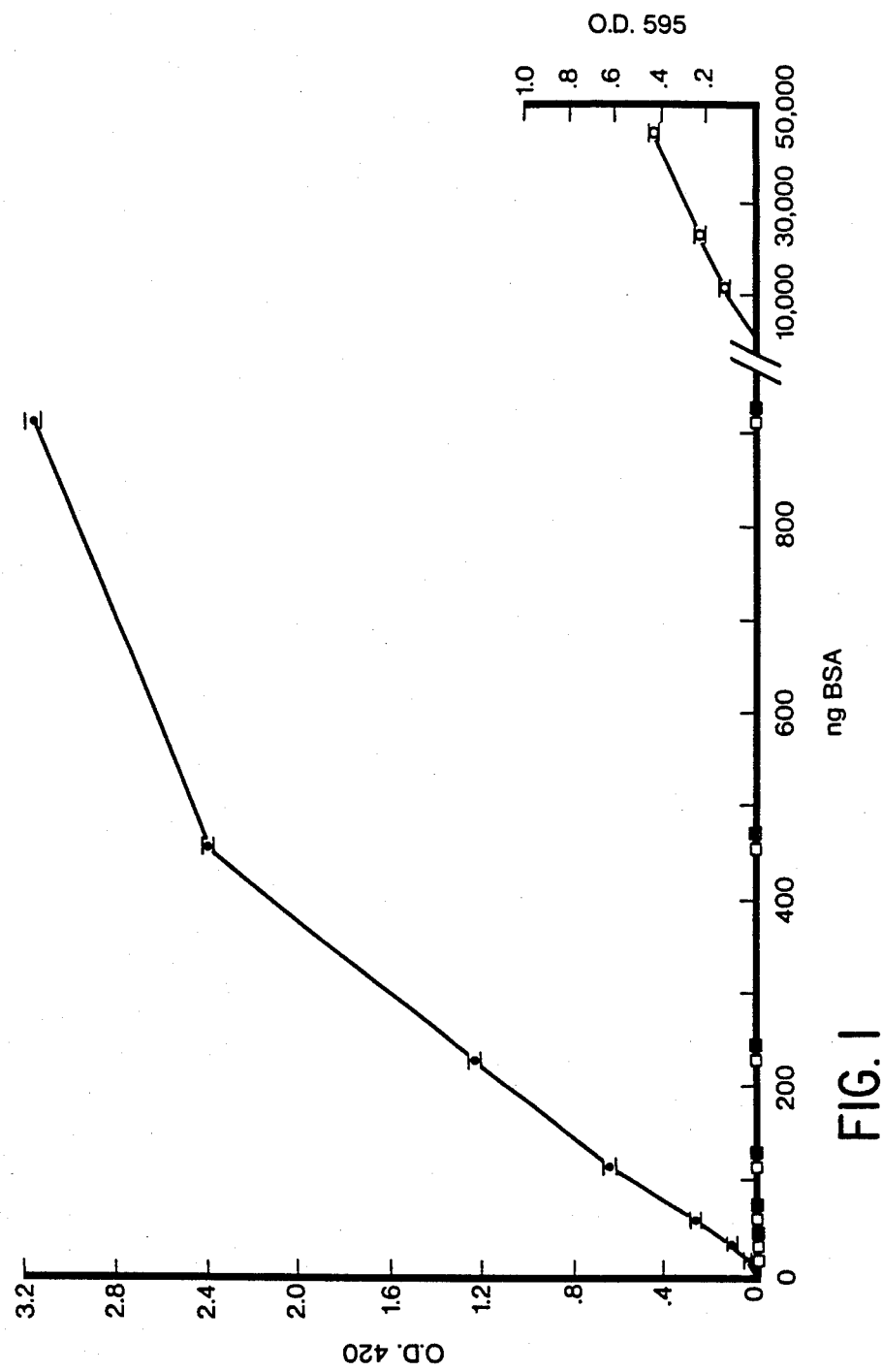
FIG. 1 depicts protein dose response curves using BSA in water containing detergent.

A specific staining procedure for the quantitation of 10–15 nanogram amounts of protein in solution is disclosed. The present assay for proteins in solution is approximately 100 times more sensitive than the corresponding Coomassie procedure (See FIG. 1). FIG. 1 depicts protein dose response curves using BSA in water containing 0.02% Tween 20. The standard silver binding procedure for protein in 0.02% Tween 20 in water ( ), the standard silver binding procedure without glutaraldehyde (□), the standard silver binding procedure with 200 μl of 2 mg/ml silver nitrate instead of ammoniacal silver ( ), the Coomassie dye binding microassay procedure ( ). The silver treated protein samples were measured at 420 nm and the Coomassie dye treated protein samples at 595 nm. Each point represents the means of 3 replicates±SEM.

Moreover, absorbance at 420 nm is a linear function of protein concentration over a range of 15 to 2000 ng for BSA and for most other standard proteins tested. Lastly, the degree of variation in silver binding by different proteins is of the same order as that observed with the Coomassie stain and the Lowry procedure. This last result was somewhat unexpected since the ability of silver to interact with proteins in a stoichiometric manner has not been observed in SDS polyacrylamide gels. (See Dion A. S. et al. above.) For example, glutaraldehyde enhancement of silver staining in polyacrylamide appears to show a direct correlation with lysine content, whereas this does not appear to be the case for glutaraldehyde-silver treatment of proteins in solution. Thus cytochrome C, in solution, with a lysine content of 13% showed a lower extinction coefficient at 420 nm than ovalbumin which has a lysine content of 4%.

Most protein solutions contain salts and other small molecules whose presence interferes with the use of silver binding as a quantitative procedure for assessing relatively small amounts of protein. Of the procedures investigated to remove a variety of such interfering molecules without significant loss of protein (present in nanogram amounts), gel permeation chromatography using beads previously drained of void volume liquid proved the most effective. The use of drained gel permeation beads for desalting protein solutions was first described by Neal and Florini in studies involving milligram amounts of protein. In the present application, it was found essential to increase the level of Tween 20 to 0.75% in order to ensure 80–100% recovery of the protein from the gel beads. Reduction of the Tween 20 concentration both in the protein sample and in the pre-equilibration buffer for the column to 0.02%, resulted in almost total adsorbance to the beads of all proteins tested at nanogram concentrations. Ten mM Trizma and 10 mM sodium carbonate were also found to be important for preventing loss of non-albumin proteins by adsorption to the gel beads.

The procedure developed (see Table 3 below) provides a simple and reproducible method for quantitating nanogram amounts of protein and can be undertaken with as little as 100 μl of sample. Because of the wide range of solutions where this method can be used we envisage that it will greatly facilitate specific activity determinations in many purification schemes.

MATERIALS AND METHODS

Reagents

Bovine serum albumin (BSA)(A-7638), bovine erythrocyte carbonic anhydrase (C-7500), iron free human transferrin (T-2252), human albumin (A-2386), ovalbumin (A-5503), horse heart cytochrome-C (C-7752), bovine pancreas insulin (I-5500), bovine pancreas ribonuclease A (R-5125), bovine pancreas trypsin (T-8253), silver nitrate (S-6506), Tween 20 (trademark) (P-1379), DL-dithiothreitol and 2-mercaptoethanol were purchased from Sigma. Glutaraldehyde (25% in water), ammonium hydroxide and sodium thiosulfate were obtained from Fisher Chemical. Bio-Gel P-2 (trademark) (100–200 mesh) was purchased from Bio-Rad. Three ml stylex disposable syringes were obtained from Pharmaseal (cat. #7200D), 30 gauge (½ inch) Yale hypodermic needles from Becton-Dickenson and Col., and both 17×100 mm (2057, clear, with cap) and 12×75 mm polystyrene tubes (2058, clear, with cap) were purchased from Falcon, C.

Protein Preparation

Except for insulin, all proteins were dissolved, at 1 mg/ml, directly into distilled water containing 0.02% Tween 20 or into phosphate-buffered saline (PBS) (1.47 mM $KH_2PO_4$, 8 mM $Na_2HPO_4$, 0.137 M NaCl, pH 7.0) containing 0.02% Tween 20. Insulin was first dissolved in 0.1 N NaOH and then diluted to 1 mg/ml with either water or PBS containing 0.02% Tween 20. Concentrations of BSA, transferrin, ovalbumin, cytochrome-C, insulin, human albumin, carbonic anhydrase, ribonuclease A and trypsin were accurately determined spectrophotometrically in a Gilford Spectrophotometer 250 based on $E^{1\%}{}_{280}$ of 6.6, 11.2, 7.4, 17.1, 10.0, 6.0, 18.0, 6.95, and 16.0 respectively. Further dilutions of these proteins were made either with PBS containing 0.02% Tween 20, distilled water containing 0.02% Tween 20 or with a buffer containing 0.75% Tween 20, 10 mM Trizma (trademark), and 10 mM sodium carbonate (buffer A).

Bio-Gel P-2 Chromatography

For removing salt and other small interfering substances from protein samples, Bio-Gel P-2, with fines removed and stored in buffer A, was poured as a thick slurry into 3 ml syringes bearing 30 gauge needles up to a bed volume of 2.0 ml. The syringes, mounted on 17×100 mm polystyrene tubes were then centrifuged at 1500 rpm (450 g) for 5 min in a Beckman TJ-6 centrifuge with a TH rotor to remove the void volume buffer. One hundred µl aliquots of protein samples in PBS, or in other solutions containing small interfering substances, were first supplemented with 10 µl of a 10×buffer A solution, then applied to the minicolumns, mounted in new collecting tubes, and allowed to sit for 5 min prior to centrifuging as above. The eluted proteins were then taken through the standard silver staining procedure for proteins in buffer A as described below. After use, columns were regenerated by filling the syringes twice with approximately 3 ml buffer A, resuspending the gel each time to release trapped air and centrifuging as above. Gels, either just used or regenerated, were stored suspended in buffer A at 4° C. For extended storage, 0.02% sodium azide was added but care was taken to wash the gel free of this antibacterial agent prior to use.

Preparation of Silver Binding Reagents

A 2.5% glutaraldehyde solution was prepared daily from the 25% stock which was stored at 4° C. Two ammoniacal silver solutions were used for this study. Both were freshly prepared each day. Ammoniacal silver solution #1, for proteins in 0.02% Tween 20 in water or in water alone, was made by first adding 1.0 ml of 4% w/v sodium hydroxide and 0.2 ml of concentrated ammonium hydroxide (29%) to 18.6 ml of distilled water. This was then followed by the dropwise addition of 0.2 ml of 20% w/v silver nitrate. Ammoniacal silver solution #2, for proteins in buffer A, was prepared by adding 1.4 ml of 20% sodium hydroxide and 0.2 ml of concentrated ammonium hydroxide to 18.2 ml of distilled water. This was then followed by 0.2 ml of 20% silver nitrate as above. Sodium thiosulfate at 30 mg/ml in distilled water was also prepared daily.

Standard Silver Binding Procedure (a) For proteins in distilled water or in distilled water containing 0.02% Tween 20. 100 µl aliquots, containing 15 to 2000 ng protein, were diluted to 1 ml with 0.9 ml of distilled water containing 0.02% Tween 20. Twenty microliters of 2.5% glutaraldehyde was then added to each sample with a Western Scientific model 810 repeater and the tubes vortexed for 2 s. To this mixture was added 200 µl of ammoniacal silver solution #1 and, following another 2 s vortexing, the tubes were allowed to sit at room temperature for 10 min. Colour development was then halted by the addition of 40 µl of 30 mg/ml of sodium thiosulfate. Absorbance at 420 nm was measured in 1 ml glass cuvettes against an appropriate reagent blank. For samples with absorbance readings over 3.0 O.D. units, equal volumes of water were added and the absorbance remeasured.

(b) For proteins in buffer A. 100 µl aliquots, containing 15 to 2000 ng protein were diluted to 1 ml with 0.9 ml of distilled water. 20 µl of 2.5% glutaraldehyde was then added as above and the tubes vortexed for 2 s. 200 µl of ammoniacal silver solution #2 was then added, the tubes vortexed and color development halted after 10 min at room temp with 40 µl of 30 mg/ml sodium thiosulfate.

Coomassie Dye-Binding Assay

The microassay as described by Bradford (above) was used without modification.

Cleaning Glass Cuvettes

If silver-treated samples were allowed to sit in cuvettes for more than a few minutes, a silver deposit formed on the cuvette walls. This could be easily removed by a brief exposure to concentrated nitric acid, followed by thorough rinsing with distilled water.

RESULTS

Optimization of Silver Binding Conditions

BSA solutions, ranging in concentration from 15 to 2000 ng/ml, were prepared in distilled water with 0.02% Tween 20 and treated first with various concentrations of glutaraldehyde and then with either silver nitrate or ammoniacal silver. These are standard reagents for silver staining proteins in SDS polyacrylamide gels. The results of these studies indicated that the presence of glutaraldehyde markedly enhanced silver deposition on protein and that ammoniacal silver was superior to silver nitrate (see FIG. 1), findings consistent with previous experience in silver staining of proteins in SDS polyacrylamide gels. Subsequent studies showed that final concentrations of 0.041% glutaraldehyde and 0.033% ammoniacal silver, gave the most useful dose response curve in the 15 to 1000 ng range (see FIG. 1). The lower limit of detection under these conditions was approximately 10 ng making this assay over 100 times more sensitive than the Coomassie dye binding procedure (see FIG. 1 for comparison). This again is reminiscent of results obtained with SDS polyacrylamide gels.

The kinetics of color development appeared to be complex and consisted of a rapid protein-specific development (from light yellow to dark brown) and a slower protein-independent darkening. The rate of the specific reaction bore an inverse relationship to the amount of protein present such that 2000 ng of protein required a substantially longer time to reach completion than 15 ng. Both the protein specific and non-specific reactions could be stopped by the addition of sodium thiosulfate as detailed in Materials and Methods. For proteins dissolved in water, 10 min as found to be a sufficient reaction time to allow 1 µg BSA to complete its specific color development and, at the same time, keep the non-specific darkening to a minimum. Optical densities were then read at 420 nm as this wavelength was found to give the highest absorbance relative to the reagent blank. Without the addition of sodium thiosulfate, the optical density of both the blank and the protein sample rose at the same rate (once the specific color reaction was over), such that the O.D. 420 of the protein sample did not change relative to the blank but made it necessary to constantly refer to the blank for correction of the slit width.

Figure 2:
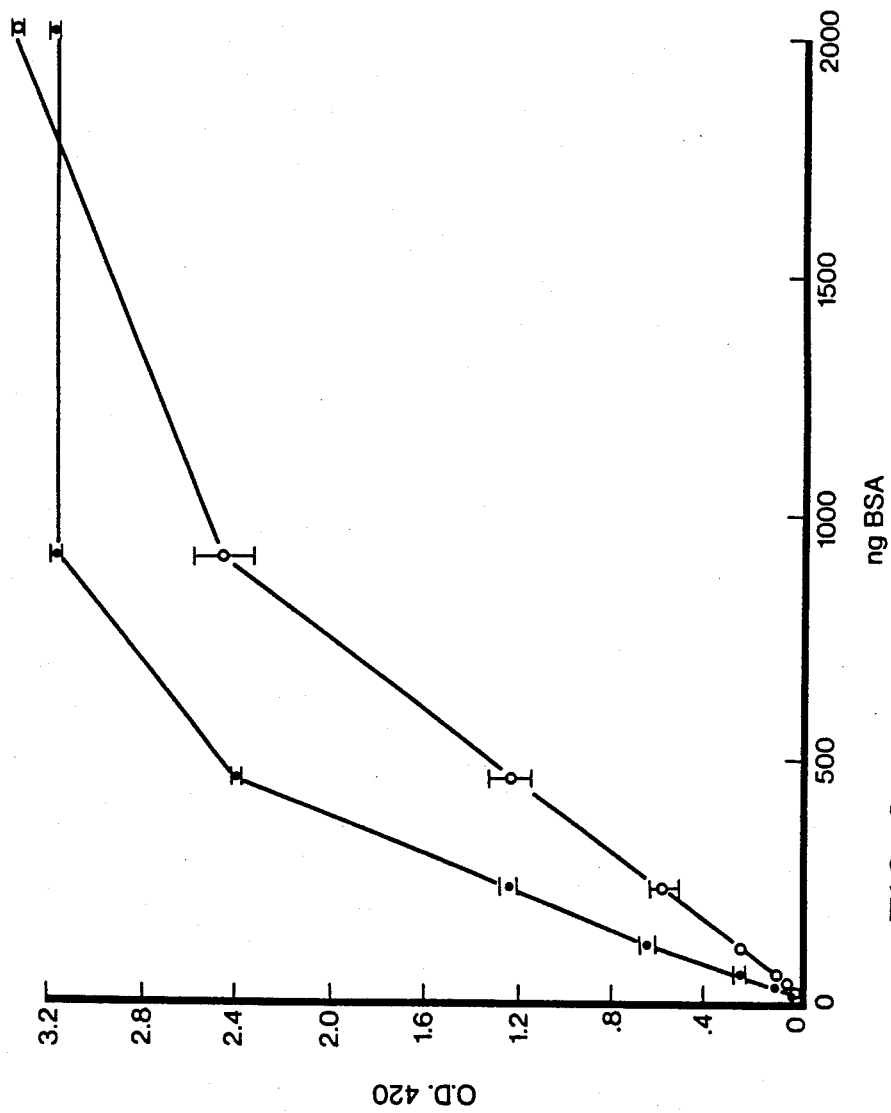
FIG. 2 depicts BSA-silver dose response curves in the presence and absence of detergent.

A common problem when dealing with very low levels of protein is that a substantial proportion of the protein may be lost by adsorption to glass and plastic surfaces of pipette and tube walls. Since we had found previously that the non-ionic detergent, Tween 20, minimized this phenomenon in other situations, the effect of its addition was tested here. Two-fold dilutions of BSA were carried out in water in the presence and absence of 0.02% Tween 20 and the resulting dilutions tested in the standard silver staining procedure using ammoniacal silver solution #1. Lower O.D. 420 readings were obtained when Tween 20 as omitted suggesting that, unless this detergent was present, some protein loss occurred (See FIG. 2). FIG. 2 depicts BSA-silver dose response curves in the presence (●) and absence (○) of 0.02% Tween 20. The standard silver binding procedure for protein in 0.02% Tween 20 in water was used. Each point represents the mean of 3 replicates±SEM.

Figure 3:
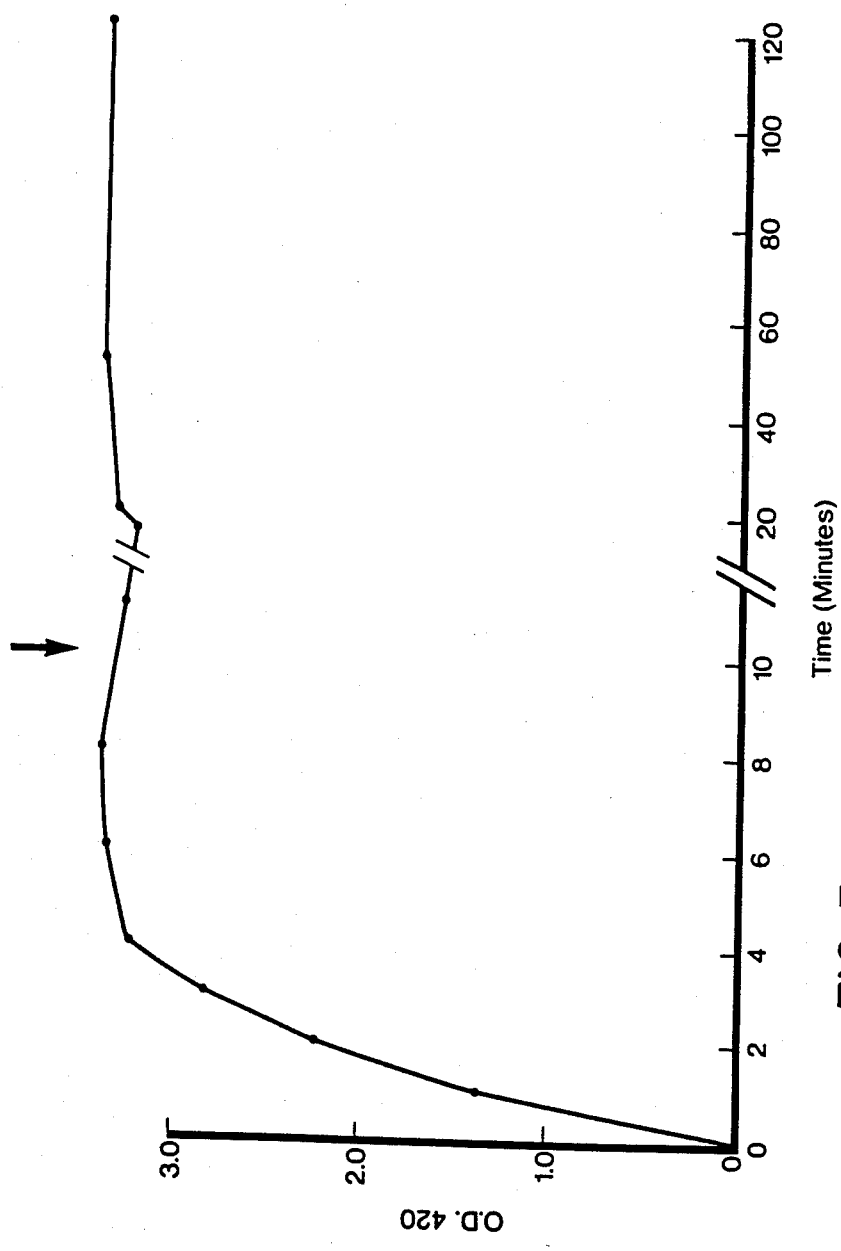
FIG. 3 depicts BSA-silver complex formation rate and color stability.

The kinetics of color development was also pH dependent, increasing with increasing pH in the pH range of 10-12. Moreover, the rate of color development was markedly reduced by the presence of various ions. For example, as little as 1.5 mM NaCl slowed color formation substantially. Higher levels of NaCl prevented protein specific color development entirely, most likely by precipitating out the silver as silver chloride. This finding posed a serious problem since most proteins for which quantitative determinations are sought are present in physiological buffers containing high concentrations of interfering ions. This potential problem could be circumvented using Bio-Gel P-2, as described below. However, for this desalting procedure to be effective, it was necessary to provide a certain minimal level of ions in the P-2 elution procedure to prevent loss of protein to the P-2 gel. Thus, studies were undertaken to find salts and detergents that would not interfere with the assay and at the same time allow high protein recoveries through P-2. This was accomplished through the use of a buffer containing 0.75% Tween 20, 10 mM Trizma, and 10 mM sodium carbonate (buffer A). This only slightly allowed the rate of specific color development and allowed high recoveries of proteins through P-2. To offset the slight retardation of the reaction rate, a second ammoniacal silver solution was prepared with a higher pH (ammoniacal silver solution #2). This second silver solution allowed completion of specifc color formation of up to 2 μg BSA in buffer A within 10 min (See FIG. 3). FIG. 3. BSA-silver complex formation rate and color stability. BSA at 2000 ng in buffer A was subjected to the standard silver binding procedure for proteins in buffer A. At 10 min, as indicated by the arrow, sodium thiosulfate was added.

Figure 4:
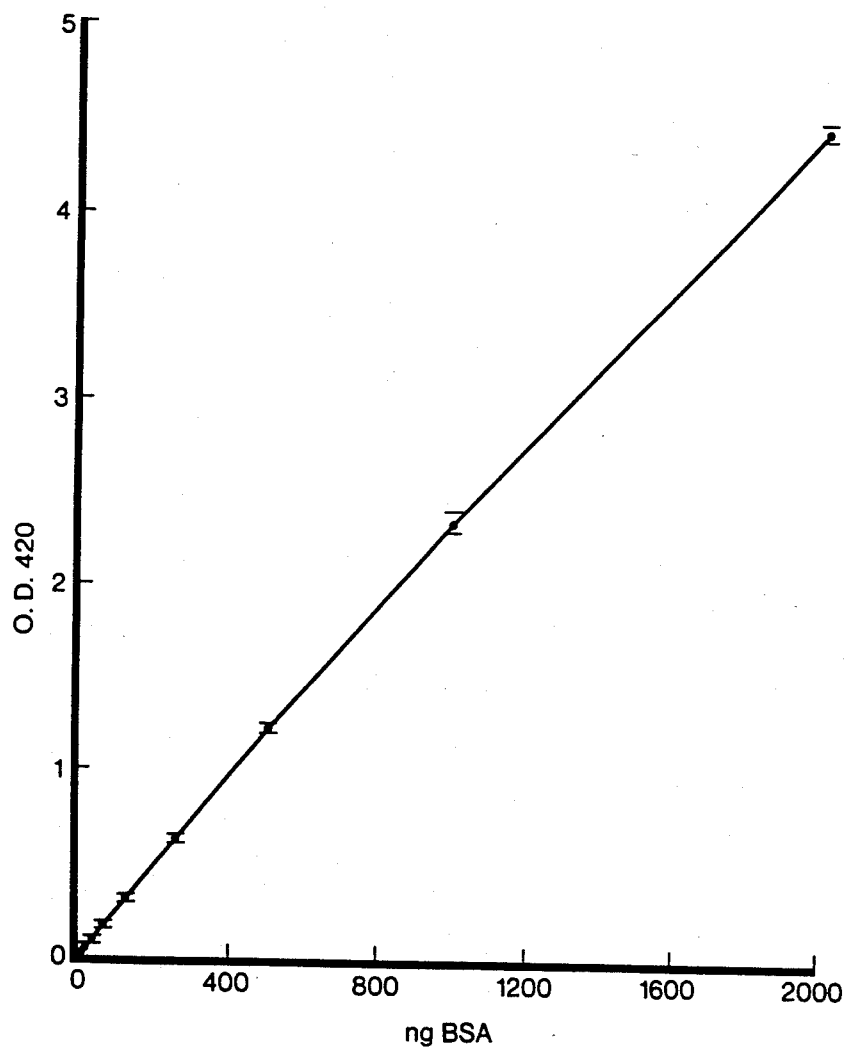
FIG. 4 depicts a BSA-silver dose response curve using buffer A and ammoniacal silver solution.

Moreover, a linear dose response curve could then be obtained for BSA in the range of 15 to 2000 ng (see FIG. 4). FIG. 4. BSA-silver dose response curve carried out using buffer A and ammoniacal silver solution #2 as detailed above. For the 2000 ng replicates, the sodium thiosulfate treated samples were diluted with an equal volume of water prior to O.D. 420 determination. Each point represents the mean of 3 replicates±SEM. Buffer A was therefore used as a diluent for all proteins in the remaining studies.

Colour development was found to be independent of light and did not require the addition of citric acid-formaldehyde, a reagent mixture commonly used to develop silver stained gels. Evaluation of the reaction obtained in different vessels showed that polystyrene tubes gave more reproducible results than either borosilicate or flint glass tubes. The use of plastic tubes also avoided the phenomenon of "mirroring" which occurred on the inside of the glass tubes when little or no protein was present.

Quantitation of the Extent of Silver Binding to Different Proteins

Figure 5:
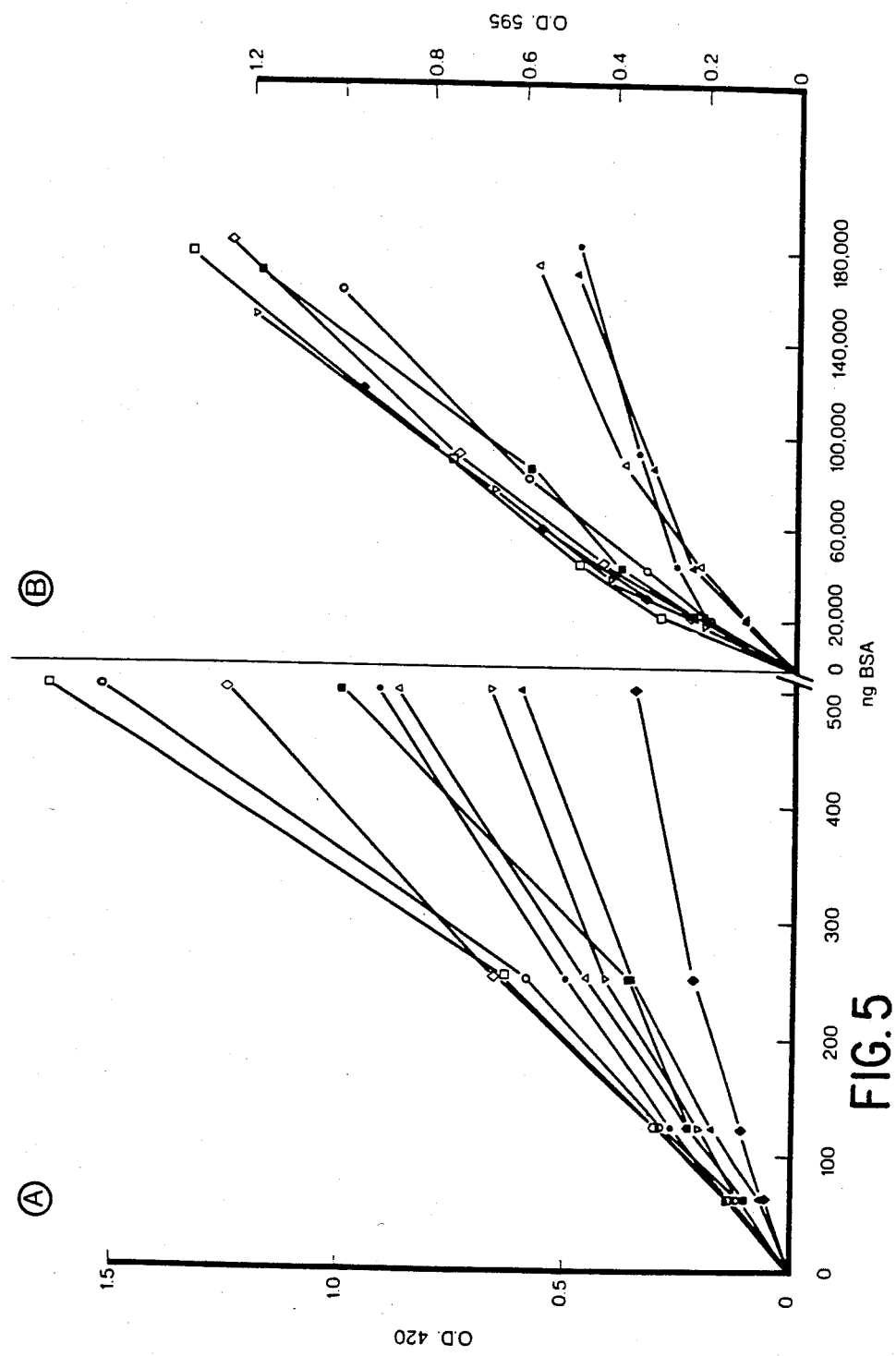
FIG. 5 depicts dose response curves for various proteins.

Dose response curves for various commercially obtained standard proteins were obtained with the silver binding assay. FIG. 5 depicts dose response curves for various proteins using, (A) the standard silver binding procedure for proteins in buffer A and, (B) the Coomassie dye binding microassay procedure. BSA (◇), transferrin (●), cytochrome C (◆), ovalbumin (Δ), human albumin (□), carbonic anhydrase (▽), ribonuclease A (●), trypsin (▲), insulin (■). Each point represents the mean of 3 replicates. For simplicity, error bars were not included but were of a similar magnitude to that seen in FIG. 4. As can be seen from the results shown in FIG. 5A some differences were observed. However, these are comparable to those seen in similar studies carried out using the Coomasie dye binding procedure (see FIG. 5B). The differences in silver binding were not due to the differing salt content of the various purchased lyophilized preparations, since they gave the same profiles after chromatography on Bio-Gel P-2.

Interference by Non-Protein Compounds

Most samples for which protein determinations are desired are present in buffers containing anions, like chloride ions, that form insoluble salts with silver. A number of procedures for dealing with these interfering substances were therefore investiated. These included dialysis against water containing 0.02% Tween 20, increasing the level of ammoniacal silver, and chromatography using ion exchange and gel filtration beads. Dialysis was discarded because it was slow, required large sample volumes and gave variable results. Increasing the level of silver to try and saturate the free interfering anions and still leave sufficient silver to react with protein did not work because of excessively high blank backgrounds. Bio-Rad AG501-X8 (trade mark) ion exchange resin beads proved very effective in removing salt ions but absorbed variable amounts of protein and therefore gave continual problems with reproducibility. The most promising approach proved to be gel filtration chromatography. However, to prevent excessive and variable losses of protein to gel beads it was necessary to provide a minimum level of ions and detergent. After testing various salts and detergents, buffer A was found to be the most effective in allowing high protein recoveries with minimal interference in the silver assay. On a bed volume basis, Bio-Gel P2 was found superior to Sephadex G10 (trade mark) for desalting. The final procedure adopted and described in Materials and Methods and further detailed in Table 3 below simply involved centrifuging protein samples through 2 ml P-2 columns pre-equilibrated with buffer A. This was found to be fast, and consistently gave between 80 and 100% recoveries for all the standard protein samples tested, including insulin (see Table 1). Thus, even small proteins with molecular weights in the range of 5000 daltons could be quantitatively recovered using this procedure.

Other compounds, generally present in protein buffer solutions, were tested to see how they affected the silver binding assay. Little or no effect was observed for protein samples containing up to 0.01 N NaOH, 0.01 N HCl, 10% glycerol, 50 mM sucrose, 20% ethanol, 1% Triton X100, 0.01% SDS or 1% Tween 20 (see Table 2). Thus, protein solutions containing only these substances could be assayed directly without prior P-2chromatography as long as the appropriate reagent blank controls were used.

Compounds that did interfere included various salts, as expected, EDTA, SDS at greater than 0.01% and the reducing agents DTT and 2-mercaptoethanol. However, these interfering substances could all be removed using P-2 chromatography (see Table 2).

A summary of the standard procedure for determining the level of protein in solutioons containing interfering substances is given in Table 3.

TABLE 1

PROTEIN RECOVERY FOLLOWING BIO-GEL P-2 CHROMATOGRAPHY

| Protein | O.D. 420 before chromatography[a] | O.D. 420 after chromatography[b] | Percent recovery |
|---|---|---|---|
| BSA | 0.538 ± .01[c] | 0.585 ± .01 | 109% |
| Transferrin | 0.596 ± .01 | 0.564 ± .02 | 95% |
| Ovalbumin | 0.534 ± .01 | 0.583 ± .07 | 109% |
| Cytochrome C | 0.163 ± .01 | 0.129 ± .02 | 80% |
| Insulin | 0.702 ± .02 | 0.725 ± .02 | 103% |
| Human Albumin | 0.554 ± .01 | 0.627 ± .03 | 113% |
| Carbonic Anydrase | 0.275 ± .01 | 0.245 ± .02 | 89% |
| Ribonuclease A | 0.531 ± .01 | 0.485 ± .02 | 91% |
| Trypsin | 0.309 ± .01 | 0.332 ± .02 | 107% |

[a]100 ul of 2.50 ug/ml solutions of each protein in buffer A was tested in the standard silver binding procedure for proteins in buffer A. The slit width of the reagent blank, consisting of 100 ul buffer A + 900 ul water, was 1.077.
[b]100 ul of 2.50 ug/ml solutions of each protein in PBS containing buffer A was centrifuged through Bio-Gel P2 as described in Materials and Methods. The eluates were tested in the standard silver binding procedure for proteins in buffer A. Aslit width of the reagent blank, consisting of 100 ul PBS containing buffer A put thru P2 + 900 ul water, was 1.088.
[c]Each value represents the mean of 3 replicates ± SEM.

TABLE 2

EFFECT OF VARIOUS PROTEIN BUFFER COMPONENTS ON THE STANDARD SILVER BINDING ASSAY

| Substance[a] + 250 ng BSA | Without Bio-Gel P2 chromatography O.D. 420 | Following Bio-Gel P2 chromatography O.D. 420 |
|---|---|---|
| Buffer A (control) | 0.54 ± .01[b] | 0.55 ± .01 |
| 0.15 M NaCl | no reaction | 0.57 ± .01 |
| 0.1 M (NH4)2SO4 | no reaction | 0.61 ± .03 |
| 0.01 N NaOH | 0.32 ± .01 | ND[d] |
| 0.01 N HCl | 0.34 ± .02 | ND |
| 0.1 M Tris-Cl* pH 7.0 | no reaction | 0.62 ± .02 |
| 10 mM EDTA | poor reaction[c] | 0.52 ± .02 |
| 10% glycerol | 0.48 ± .01 | ND |
| 50 mM sucrose | 0.48 ± .02 | ND |
| 0.1 M 2-mercaptoethanol | no reaction | 0.68 ± .02 |
| 0.1 M dithiothreitol | no reaction | 0.62 ± 0.2 |
| 20% ethanol | 0.62 ± .01 | ND |
| 1% Triton X100* | 0.65 ± .01 | ND |
| 0.01% SDS | 0.55 ± .02 | ND |
| 0.1 SDS | poor reaction | 0.57 ± .03 |

TABLE 2-continued

EFFECT OF VARIOUS PROTEIN BUFFER COMPONENTS ON THE STANDARD SILVER BINDING ASSAY

| Substance[a] + 250 ng BSA | Without Bio-Gel P2 chromatography O.D. 420 | Following Bio-Gel P2 chromatography O.D. 420 |
|---|---|---|
| 0.25% Tween 20 | 0.40 ± .01 | ND |

[a]100 ul of all substances, in buffer A containing 250 ng BSA, were tested using the standard silver binding procedure for proteins in buffer A. Slit widths were determined using 100 ul of the substances in buffer A without protein.
[b]Each value is the mean of 2 replicates ± SEM.
[c]Poor reactions are defined as those in which the protein specific color development is very slow such that the non-specific darkening obscures it.
[d]ND, not determined because deemed unnecessary.
*Trademarks.

TABLE 3

STANDARD SILVER BINDING PROCEDURE FOR PROTEINS IN BUFFERS CONTAINING INTERFERING SUBSTANCES

1. Add 10 ul 10 × buffer A to 100 ul buffer X (reagent blank).
2. Add 10 ul 10 × buffer A to 100 ul protein sample in buffer X.
3. Centrifuge the above 2 samples at 450 g for 5 min through 2 ml Bio-Gel P2 columns which have been pre-equilibrated with buffer A and then drained of void volume liquid.
4. Prepare the standard curve by making 2 fold serial dilutions of 100 ul 20 ug/ml BSA in buffer A (i.e. 2000, 1000, 500, 250, 125, 62, 31, 15, 0 ng).[a]
5. Add 0.9 ml distilled water to all samples to bring total volume to 1.0 ml.
6. Add 20 ul 2.5% glutaraldehyde to all samples and vortex 2 s.
7. Add 200 ul ammoniacal silver solution #2 to all samples and vortex 2 s.
8. After exactly 10 min, add 40 ul 30 mg/ml sodium thiosulfate.
9. Using the appropriate reagent blanks, measure the O.D. 420 of the samples within 2 hrs.

[a]It is first essential to determine whether BSA dilutions in buffer A give the same O.D. 420 readings as BSA dilutions in buffer X + A chromatographed through P2. If this is not the case, then the BSA standards must be in buffer X + A and put through P2 in an identical fashion to the tested samples.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

I claim:

1. A method of measuring the concentration of protein in solution comprising:
   (a) treating a protein containing sample solution with a silver-on-protein deposition enhancement agent;
   (b) exposing the treated protein containing sample solution of step (a) above to a silver compound to develop a protein specific colour with the protein in the sample solution by protein-silver binding;
   (c) terminating the exposure reaction of step (b) above after sufficient protein specific colour development and a minimum of non-specific darkening has occurred; and
   (d) measuring the optical density of the exposure terminated protein containing sample solution of step (c) above as a measure of the protein concentration above.

2. A method according to claim 1 wherein the enhancement agent is a dialdehyde.

3. A method according to claim 1 wherein the enhancement agent is glutaraldehyde.

4. A method according to claim 1 wherein the silver compound is ammoniacal silver.

5. A method according to claim 3 wherein the silver compound is ammoniacal silver.

6. A method according to claim 1, 2 or 3 wherein the silver compound is silver nitrate.

7. A method according to claim 4 or 5 wherein said protein containing sample solution contains colour development interfering ions and a buffer solution is added to the protein containing sample solution prior to step (a).

8. A method according to claim 4 or 5 including the step of removing any colour development interfering ions in the protein containing sample solution utilizing gel filtration beads prior to step (a).

9. A method according to claim 4 or 5 including the steps of adding minimum levels of ions and detergent to the protein containing sample solution to minimize protein loss in gel filtration beads and removing any colour development interfering ions in the protein containing sample solution utilizing gel filtration beads prior to step (a).

10. A method according to claim 4 or 5 wherein the concentration of the protein present in the protein containing sample solution is in the range 10–2000 nanograms.

11. A method according to claim 4 and 5 wherein the optical density of step (d) is measured at 420 nm.

12. A method according to claim 1, 2 or 3 wherein the colour development is terminated in step (c) by adding sodium thiosulfate to the protein containing sample solution.

13. A method according to claim 4 or 5 wherein the colour development is terminated in step (c) by adding sodium thiosulfate to the protein containing sample solution.

14. A method according to claim 1, 2 or 3 wherein the colour development is terminated in step (c) at about 10 minutes after commencement of step (b).

15. A method according to claim 4 or 5 wherein the colour development is terminated in step (c) at about 10 minutes after commencement of step (b).

16. A method of measuring the concentration of protein in solution comprising:
  (a) treating a protein containing sample solution with glutaraldehyde;
  (b) exposing the glutaraldehyde treated protein containing sample solution to ammoniacal silver to develop a protein specific colour with the protein in the sample solution by protein-silver binding;
  (c) permitting the colour development to proceed for about 10 minutes;
  (d) terminating the colour development with sodium thiosulfate; and
  (e) measuring the optical density of the protein containing sample solution at 420 nm as a measure of the protein concentration.

17. A method according to claim 16 wherein the protein containing sample solution includes analysis interfering ions and is pretreated with drained gel permeation beads to remove such ions.

18. A method of measuring the concentration of protein in solution comprising:
  (a) diluting a 100 μl aliquot of a solution containing 15 to 2000 ng protein to 1 ml with 0.9 ml of distilled water containing 0.02% non-ionic detergent;
  (b) adding 20 μl of 2.5% glutaraldehyde to the sample solution prepared by step (a) above;
  (c) adding 200 μl of an ammoniacal silver solution prepared by adding 1.0 ml of 4% w/v sodium hydroxide and 0.2 ml of ammonium hydroxide (29%) to 18.6 ml of distilled water followed by dropwise addition of 0.2 ml of 20% w/v silver nitrate to the sample solution to develop a protein specific colour with the protein in the sample solution by protein-silver binding;
  (d) permitting colour development caused by protein-silver binding to proceed for about 10 minutes;
  (e) adding 40 μl of 30 mg/ml of sodium thiosulfate to the sample solution to terminate the colour development; and
  (f) measuring the optical density of the sample solution at 420 nm as a measure of the protein concentration.

19. A method of measuring the concentration of protein in a buffer solution containing an analysis interfering substance comprising:
  (a) pretreating a solution containing 15 to 2000 ng protein and an analysis interfering substance in a buffer containing 0.75% non-ionic detergent, 10 mM Trizma and 10 mM sodium carbonate utilizing gel filtration chromatography to remove the analysis interfering substance;
  (b) diluting a 100 μl aliquot of said pretreated solution to 1 ml with 0.9 ml distilled water;
  (c) adding 20 μl of 2.5% glutaraldehyde to the sample solution prepared by step (b) above;
  (d) adding 200 μl of an ammoniacal silver solution prepared by adding 1.4 ml of 20% sodium hydroxide and 0.2 ml of concentrated ammonium hydroxide (29%) to 18.2 ml of distilled water followed by dropwise addition of 0.2 ml of 20% w/v silver nitrate to the sample solution to develop a protein specific colour with the protein in the sample solution by protein-silver binding;
  (e) permitting colour development caused by protein-silver binding to proceed for about 10 minutes;
  (f) adding 40 μl of 30 mg/ml of sodium thiosulfate to the sample solution to terminate colour development; and
  (g) measuring the optical density of the sample solution at 420 nm as a measure of the protein concentration.

* * * * *